US007071225B2

(12) United States Patent
Hellberg et al.

(10) Patent No.: US 7,071,225 B2
(45) Date of Patent: Jul. 4, 2006

(54) ARYLAMINOPROPANE ANALOGUES AND THEIR USE FOR THE TREATMENT OF GLAUCOMA

(75) Inventors: Mark R. Hellberg, Arlington, TX (US); Abdelmoula Namil, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/723,208

(22) Filed: Nov. 26, 2003

(65) Prior Publication Data
US 2004/0110791 A1 Jun. 10, 2004

Related U.S. Application Data

(63) Continuation of application No. PCT/US02/16842, filed on May 30, 2002.

(60) Provisional application No. 60/295,426, filed on Jun. 1, 2001.

(51) Int. Cl.
*A61K 31/38* (2006.01)
*C07D 471/00* (2006.01)

(52) U.S. Cl. .................. 514/443; 546/167; 549/55; 562/442

(58) Field of Classification Search ............... 562/442; 546/167; 549/55; 514/443
See application file for complete search history.

(56) References Cited

U.S. PATENT DOCUMENTS

| | | | |
|---|---|---|---|
| 4,690,931 A | 9/1987 | Wick et al. | 514/317 |
| 5,151,444 A | 9/1992 | Ueno et al. | 514/530 |
| 5,296,504 A | 3/1994 | Stjernschantz et al. | 514/530 |
| 5,352,708 A | 10/1994 | Woodward et al. | 514/729 |
| 5,422,368 A | 6/1995 | Sternschantz et al. | 514/530 |
| 5,494,928 A | 2/1996 | Bös | 514/415 |
| 5,571,833 A | 11/1996 | Kruse et al. | 514/414 |
| 5,578,612 A | 11/1996 | Macor et al. | 514/323 |
| 5,874,477 A | 2/1999 | McConnell et al. | 514/657 |
| 5,889,052 A | 3/1999 | Klimko et al. | 514/530 |
| 5,902,815 A | 5/1999 | Olney et al. | 514/285 |
| 6,548,493 B1 | 4/2003 | Robichaud et al. | 514/212.05 |
| 6,552,017 B1 | 4/2003 | Robichaud et al. | 514/219 |
| 6,713,471 B1 | 3/2004 | Robichaud et al. | 514/211.1 |
| 2004/0034015 A1 | 2/2004 | Robichaud et al. | 514/219 |

FOREIGN PATENT DOCUMENTS

| | | |
|---|---|---|
| EP | 0771563 A2 | 5/1997 |
| WO | WO 92/20338 | 11/1992 |
| WO | WO 94/13275 | 6/1994 |
| WO | WO 97/33579 | 9/1997 |
| WO | WO 98/18458 | 5/1998 |
| WO | WO 98/31354 | 7/1998 |
| WO | WO 00/12475 | 3/2000 |
| WO | WO 00/12510 | 3/2000 |
| WO | WO 00/16761 | 3/2000 |
| WO | WO 00/35922 | 6/2000 |
| WO | WO 00/44753 | 8/2000 |

OTHER PUBLICATIONS

Clare et al., Journal of Medicinal Chemistry, vol. 41, No. 20 (1998).*
Ichiro et al., "Studies on the synthesis of 2-substituted-1-naphthols and 7-substituted-8-quinolinols," *Chem. Abstr.* vol. 108, 186616g, pp. 695 (1988).
Horii et al., "Synthetic Studies on Anthracyclinones, IX Lithiation of N,N-Dimethyl-napthhalenemethylamines and a New Synthetic Pathway to 2,3-Napthalides," *Chem. Pharma. Bull.* Vo. 19(6), pp. 1245-1256 (1971).
IOVS, *Aqueous Humor Dynamics I*, vol. 39(4), S488, 2236-B93, (1998).
Glennon, et al., "Binding of Substituted and Conformationally Restricted Derivatives of N-(3-Phenyl-n-propyl)-1-phenyl-2-aminopropane at σ-Receptors," *J. Med. Chem*, vol. 34, pp. 855-1859 (1991).
R. Howe, "β-Adrenergic Blocking Agents. VI, Pronethalol and Propranolol Analogs with Alkyl Substituents in the Alkanol Side Chain." *J. Med. Chem.* vol. 12, pp. 642-646 (1969).
Govindachari et al., "Synthesis of 3-Methyl Isoquinolines," *J. Org. Chem.* vol. 18, pp. 1253-1262 (1953).
Griffin, et al., "Pharmacological Characterization of an FP Prostaglandin Receptor on Rat Vascular Smooth Muscle Cells (A7r5) Coupled to Phosphoinositide Turnover and Intracellular Calcium Mobilization," *J. Pharmacol. Expt. Ther.* vol. 286, pp. 411-418 (1998).
Johnson et al., Binding to the Serotonin 5-HT2 Receptor by the Enantiomers of $125_{I\text{-}DOI}$, *Neuropharmacology*, vol. 26, No. 12, pp. 1803-1806 (1987).
Osborne, et al. "Do Beta-Adrenoceptors and Serotonin 5-$HT_{1A}$ Receptors Have Similar Functions in the Control of Intraocular Pressure in the Rabbit?" *Ophthalmologica*, vol. 210, pp. 308-314 (1996).
Fiorella, "Role of 5-$HT_{2A}$ and 5-$HT_{2C}$ receptors in the stimulus effects of hallucinogenic drugs II: reassessment of LSD false positives," *Psychopharmacology*, vol. 121:357-363, 1995.
Bowen et al., "Nonlinear regression using spreadsheets," *Trends Pharmacol. Sci.*, vol. 16, pp. 413-417 (1995).
Wang, et al., "Effect of 5-methylurapidil, an $\alpha_{1a}$-adrenergic antagonist and 5-hydroxytryptamine$_{1a}$ agonist, on aqueous humor dynamics in monkeys and rabbits" *Current Eye Research*, vol. 16(8) pp. 769-775 (1997).

(Continued)

*Primary Examiner*—Kamal A. Saeed
(74) *Attorney, Agent, or Firm*—Kilyk & Bowersox, P.L.L.C.

(57) ABSTRACT

Arylaminopropane analogues are disclosed. Also disclosed are methods for the lowering and controlling of normal or elevated intraocular pressure as well as a method for the treatment of glaucoma using compositions containing one or more of the compounds of the present invention.

13 Claims, No Drawings

OTHER PUBLICATIONS

Nabih, et al.. "Synthesis of (Heterocyclicamino) aminoalkylnaphthols and Reduced Tetrahydro Derivatives for Possible Antimalarial Activity," J. of Pharm. Sciences, vol. 61, No. 9, pp. 1500-1501 (1972).

Clare, "The Frontier Orbital Phase Angles: Novel QSAR Descriptors for Benzene Derivatives, Applied to phenylalkylamine Hallucinogens," J. Med. Chem. vol. 41, pp. 3845-3856 (1998).

International Search Report for PCT/US02/16842 dated Aug. 19, 2002.

Shulgin et al., "A chemical love story," Transform Press, Berkeley, CA (1991), #86, reprinted online at www.erowid.org/library/books_online/pihkal/pihlal086.

* cited by examiner

ARYLAMINOPROPANE ANALOGUES AND THEIR USE FOR THE TREATMENT OF GLAUCOMA

This application is a continuation of International Patent Application No. PCT/US02/16842 filed May 30, 2002 and in turn claims the benefit of U.S. Provisional Patent Application No. 60/295,426, filed Jun. 1, 2001, incorporated in its entirety by reference herein.

BACKGROUND OF THE INVENTION

The present invention relates to various arylaminopropane analogues. These novel compounds are useful for lowering and controlling normal or elevated intraocular pressure (IOP) and for treating glaucoma.

The disease state referred to as glaucoma is characterized by a permanent loss of visual is function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be a high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP 0771563A2 (Mano, et al.). Osborne, et al. (Ophthalmologica, Vol. 210:308–314, 1996) teach that 8-hydroxydipropylaminotetralin (8-OH-DPAT) (a 5-$HT_{1A}$ agonist) reduces IOP in rabbits. Wang, et al. (Current Eye Research, Vol. 16(8):769–775, August 1997, and IVOS, Vol. 39(4), S488, March, 1998) indicate that 5-methylurapidil, an $\alpha_{1A}$ antagonist and 5-$HT_{1A}$ agonist lowers IOP in the monkey, but due to its $\alpha_{1A}$ receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These antimigraine compounds are 5-$HT_{1B,D,E,F}$ agonists, e.g., sumatriptan and naratriptan and related compounds.

It has been found that serotonergic compounds which possess agonist activity at 5-$HT_2$ receptors effectively lower and control normal and elevated IOP and are useful for treating glaucoma, see commonly owned co-pending application, PCT/US99/19888, incorporated in its entirety by reference herein. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders. U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO 98/31354 relates to 5-$HT_{2B}$ agonists for the treatment of depression and other CNS conditions. WO 00/12475 relates to indoline derivatives and WO 00/12510 and WO 00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivates as 5-$HT_{2C}$ agonists for the treatment of obsessive compulsive disorder, depression, eating disorders, and other disorders involving the CNS. WO 00/77002 and WO 00/77010 relate to certain substituted tetracyclic pyrido[4,3-b]indoles as 5-$HT_{2C}$ agonists with utility for the treatment of central nervous system disorders including obesity, anxiety, depression, sleep disorders, cephalic pain, and social phobias among others. Agonist response at the 5-$HT_{2C}$ receptor is reported to be the primary activity responsible for hallucinogenic activity, with some lesser involvement of the 5-$HT_{2C}$ receptor possible [Psychopharmacology, Vol. 121: 357, 1995].

All the patents and publications mentioned above and throughout are incorporated in their entirety by reference herein.

1-Methyl-2-naphthalen-2-yl-ethylamine has been explored as a possible ligand for the sigma receptor [*J. Med. Chem*, 34, 1855 (1991)]. 2-amino-1-naphthalen-2-yl-propan-1-ol isomers have been explored as possible β-adrenergic receptor antagonists [*J. Med. Chem.* 12, 642 (1969)]. A synthesis of 2-amino-1-(1-methoxy-naphthalen-2-yl)-propan-1-ol has been reported [*J. Org. Chem.* 18, 1253 (1953)]. Studies on the synthesis of certain 2-substituted-1-naphthols, such as 2-amino-1-(1-methoxy-naphthalen-2-yl)-propan-1-ol, have been reported [*Kyushu Kyoritsu Daigaku Kenkyu Hokoku, Kogakubu,* 11, 1–8 (1987), cited in *Chem. Abstr.* 108:186616 (1988)].

Accordingly, there is a need to provide new compounds which avoid the disadvantages described above and which provide increased chemical stability and a desired length of therapeutic activity, for instance, in decreasing intraocular pressure and treating glaucoma.

SUMMARY OF THE PRESENT INVENTION

A feature of the present invention is to provide novel compounds which are 5-$HT_2$ agonists.

Another feature of the present invention is to provide compounds which have increased chemical stability and which are useful in lowering and controlling normal or elevated intraocular pressure and/or treating glaucoma.

Another feature of the present invention is to provide compounds which provide a desired level of therapeutic activity in lowering and controlling normal or elevated intraocular pressure and/or treating glaucoma.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a compound having the Formula I:

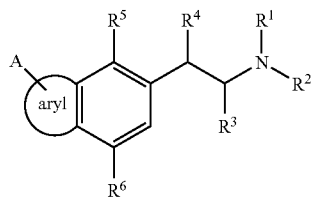

In this formula, $R^1$, $R^2$, $R^3$ are independently chosen from hydrogen or an alkyl group, such as $C_{1-3}$ alkyl;

$R^4$ is H, $OR^1$;

$R^5$ is $OCON(R^1,R^2)$, $OCOR^1$, or $OR^7$;

$R^6$ is H, $OR^7$, $CONR^1R^2$, $CH_2OR^7$, $CO_2R^1R^2$, or $N(R^1R^2)$, with the proviso that both $R^5$ and $R^6$ are not H;

Aryl represents an aryl group such as phenyl, pyridinyl, thienyl;

A is chosen from hydrogen, an alkyl group such as $C_{1-4}$alkyl, $C(=O)OR^7$, $OR^7$, $CR^7$, $C(=O)NR^1R^2$, $SO_2(NR^1R^2)$, halogen, or $CF_3$; and $R^7$ is H, an alkyl group such as $C_{1-3}$alkyl, $C_{1-3}CONR^1R^2$, $C_{1-3}N(R^1R^2)$, $C_{1-3}CO_2H$, $C_{1-3}CO_2C_{1-3}$alkyl; or a substituted alkyl such as $C_{1-3}$alkyl (which can be substituted with hydroxyl, $C_{1-3}CO_2C_{1-3}$alkyl, $C_{1-3}CON(C_{1-3}$alkyl$)_2$, $C(=NH)NH_2$, $NHC(=NH)NH_2$, or $C_{1-3}$alkoxy).

The present invention further relates to methods to lower and/or control normal or elevated intraocular pressure by administering an effective amount of a composition containing a compound having Formula I as described above.

The present invention also relates to a method for treating glaucoma which involves administering an effective amount of a composition containing a compound having Formula I as described above.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to a variety of compounds which are useful according to the present invention. These compounds are generally represented by the following Formula I.

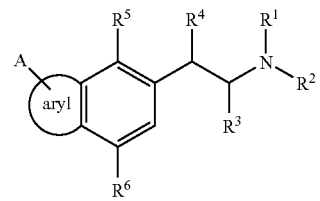

In this formula, $R^1$, $R^2$, $R^3$ are independently chosen from hydrogen or an alkyl group, such as $C_{1-3}$ alkyl;

$R^4$ is H, $OR^1$;

$R^5$ is $OCON(R^1,R^2)$, $OCOR^1$, or $OR^7$;

$R^6$ is H, $OR^7$, $CONR^1R^2$, $CH_2OR^7$, $CO_2R^1R^2$, or $N(R^1R^2)$, with the proviso that both $R^5$ and $R^6$ are not H;

Aryl represents at least one aryl group such as phenyl, pyridinyl, thienyl, and the like. The aryl group can be substituted or unsubstituted. Other examples include, but are not limited to furanyl, thiazinyl, thiazolyl, isoxazolyl, isothiazolyl.

A is chosen from hydrogen, an alkyl group such as $C_{1-4}$alkyl, $C(=O)OR^7$, $OR^7$, $CR^7$, $C(=O)NR^1R^2$, $SO_2(NR^1R^2)$, halogen, or $CF_3$;

$R^7$ is H, an alkyl group such as $C_{1-3}$alkyl, $C_{1-3}CONR^1R^2$, $C_{1-3}N(R^1R^2)$, $C_{1-3}CO_2H$, $C_{1-3}CO_2C_{1-3}$alkyl; or a substituted alkyl such as $C_{1-3}$alkyl (which can be substituted with hydroxyl, $C_{1-3}CO_2C_{1-3}$alkyl, $C_{1-3}CON(C_{1-3}$alkyl$)_2$, $C(=NH)NH_2$, $NHC(=NH)NH_2$, or $C_{1-3}$alkoxy).

Certain compounds of Formula I can contain one or more chiral centers. The present invention contemplates all enantiomers, diastereomers, and mixtures thereof.

In the above definitions, the total number of carbon atoms in a substituent group is indicated by the $C_{i-j}$ prefix where the numbers i and j define the number of carbon atoms. This definition includes straight chain, branched chain, and cyclic alkyl or (cyclic alkyl) alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

The compounds of the present invention can be prepared using the techniques shown in the Examples below. The reaction schemes set forth in the Examples set forth the procedures to make the compounds used in the Examples and provide the procedures to use in order to modify and produce the remaining compounds encompassed by the present invention.

The compounds of the present invention can be used to lower and control IOP including IOP associated with normotension glaucoma, ocular hypertension, and glaucoma in warm blooded animals including humans. The compounds are preferably formulated in pharmaceutical compositions which are preferably suitable for topical delivery to the eye of the patient.

The compounds of this invention, Formula I, can be incorporated into various types of ophthalmic formulations for delivery to the eye (e.g., topically, intracamerally, or via an implant). The compounds are preferably incorporated into topical ophthalmic formulations for delivery to the eye. The compounds may be combined with ophthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), α1 antagonists (e.g., nipradolol), α2 agonists (e.g. iopidine and brimonidine), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368; and 5,151,444, "hypotensive lipids" (e.g., bimatoprost and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 60/203,350, and appropriate compounds from WO 94/13275, including memantine.

In the formulas described above, the alkyl group can be straight-chain, branched or cyclic and the like. Halogen includes Cl, Br, F, or I. Alkoxy is understood as an alkyl group bonded through an oxygen atom.

The compounds of the present invention preferably function as 5-$HT_2$ agonists and preferably do not enter the CNS. In more detail, the particular compounds of the present invention have incorporated into their structure a phenolic hydroxyl group which is considered comparable to that of serotonin and thus the compounds of the present invention preferably do not cross the blood-brain barrier and enter the brain. Compounds having the ability to be a 5-$HT_2$ agonist are beneficial for controlling IOP as well as the treatment of glaucoma as shown in International Published Patent Application No. WO 00/16761, incorporated in its entirety by reference herein.

The compounds of the present invention preferably provide increased chemical stability and preferably achieve the desired level of therapeutic activity which includes a lowering or controlling of IOP.

The compounds of the present invention can be used in controlling or lowering IOP in warm blooded animals including humans. Preferably, an effective amount of the compound is administered to the patient such that the IOP is controlled or lowered to acceptable levels. Furthermore, the compounds of the present invention can be used to treat glaucoma in warm blooded animals, including humans, by administering an effective amount of the compound to a patient in need of such treatment to treat the glaucoma.

A method to activate or bind to serotonin receptors comprising administering an effective amount of at least one compound of Formula I to a patient is a further embodiment of the present application. The dosage amounts and other optional components can be used in this embodiment as well.

The following examples are given to illustrate the preparation of compounds that are the subject of the present invention but should not be construed as implying limitations to the claims.

Method 1

5-$HT_2$ Receptor Binding Assay

To determine the affinities of serotonergic compounds at the 5-$HT_2$ receptors, their ability to compete for the binding of the agonist radioligand [$^{125}$I]DOI to brain 5-$HT_2$ receptors is determined as described below with minor modification of the literature procedure [Neuropharmacology, 26, 1803 (1987)]. Aliquots of post mortem rat or human cerebral cortex homogenates (400 μl) dispersed in 50 mM TrisHCl buffer (pH 7.4) are incubated with [$^{125}$I]DOI (80 pM final) in the absence or presence of methiothepin (10 μM final) to define total and non-specific binding, respectively, in a total volume of 0.5 ml. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the $IC_{50}$ or $K_i$ value.

Method 2

5-$HT_2$ Functional Assay: Phosphoinositide (PI) Turnover Assay

The relative agonist activity of serotonergic compounds at the 5-$HT_2$ receptor can be determined in vitro using the ability of the compounds to stimulate the production of [$^3$H]inositol phosphates in [$^3$H]myo-inositol-labeled A7r5 rat vascular smooth muscle cells by their ability to activate the enzyme phospholipase C. These cells are grown in culture plates, maintained in a humidified atmosphere of 5% $CO_2$ and 95% air and fed semi-weekly with Dulbecco's modified Eagle medium (DMEM) containing 4.5 g/L glucose and supplemented with 2 mM glutamine, 10 μg/ml gentamicin, and 10% fetal bovine serum. For the purpose of conducting the phosphoinositide (PI) turnover experiments, the A7r5 cells are cultured in 24-well plates as previously [J. Pharmacol. Expt. Ther. 286, 411 (1998)]. Confluent cells are exposed for 24–30 hrs to 1.5 µCi [³H]-myo-inositol (18.3 Ci/mmol) in 0.5 ml of serum-free medium. Cells are then rinsed once with DMEM/F-12 containing 10 mM LiCl prior to incubation with the test agent (or solvent as the control) in 1.0 mL of the same medium for 1 hr at 37° C., after which the medium is aspirated and 1 ml of cold 0.1 M formic acid added to stop the reaction. The chromatographic separation of [³H]-inositol phosphates ([³H]-IPs) on an AG-1-X8 column is performed as previously described [J. Pharmacol. Expt. Ther. 286, 411 (1998)] with sequential washes with $H_2O$ and 50 mM ammonium formate, followed by elution of the total [³H]-IPs fraction with 1.2 M ammonium formate containing 0.1 M formic acid. The eluate (4 mL) is collected, mixed with 15 ml scintillation fluid, and the total [³H]-IPs determined by scintillation counting on a beta-counter. Concentration-response data are analyzed by the sigmoidal fit function of the Origin Scientific Graphics software (Microcal Software, Northampton, Mass.) to determine agonist potency ($EC_{50}$ value) and efficacy (Emax). Serotonin (5-HT) is used as a positive control (standard) agonist compound and the efficacy of test compounds is compared to that of 5-HT (set at 100%). The concentration of the compound needed to stimulate the production of [³H]-IPs by 50% of the maximum response is termed the $EC_{50}$ value.

The above procedures were used to generate the data shown in Table 1.

TABLE 1

5-HT₂ Receptor Binding and Functional Data

| Compound | $IC_{50}$, nM | $EC_{50}$, nM | Efficacy ($E_{max}$, %) |
|---|---|---|---|
| Example 1 | 0.73 | 238 | 118 |
| Example 2 | 1.2 | 6,810 | 113 |
| 5-HT | 0.941 | 469 | 100 |

Method 2

5-HT₂ Functional Assay: $[Ca^{2+}]_i$ Mobilization

The receptor-mediated mobilization on intracellular calcium ($[Ca^{2+}]_i$) was studied using the Fluorescence Imaging Plate Reader (FLIPR) instrument. Rat vascular smooth muscle cells, A7r5, were grown in a normal media of DMEM/10% FBS and 10 µg/mL gentamycin. Confluent cell monolayers were trypsinized, pelleted, and re-suspended in normal media. Cells were seeded in a 50 µL volume at a density of 20,000 cells/well in a black wall, 96-well tissue culture plate and grown for 2 days.

On the day of the experiment, one vial of FLIPR Calcium Assay Kit dye was re-suspended in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 mL) to each well of the 96-well plate and incubated with dye for 1 h at 23° C.

Typically, test compounds were stored at 25 µM in 50% DMSO/50% Ethanol solvent. Compounds were diluted 1:50 in 20% DMSO/20% Ethanol. For "hit" screening, compounds were further diluted 1:10 in FLIPR buffer and tested at a final concentration of 10 µM. For dose-response experiments, compounds were diluted 1:50 in FLIPR buffer and serially diluted 1:10 to give a 5- or 8-point dose-response curve.

The compound plate and cell plate were placed in the FLIPR instrument. At the beginning of an experimental run, a signal test was performed to check the basal fluorescence signal from the dye-loaded cells and the uniformity of the signal across the plate. The basal fluorescence was adjusted between 8000–12000 counts by modifying the exposure time, the camera F-stop, or the laser power. Instrument settings for a typical assay were the following: laser power 0.3–0.6 W, camera F-stop F/2, and exposure time 0.4 sec. An aliquot (25 µL) of the test compound was added to the existing 100 µL dye-loaded cells at a dispensing speed of 50 µL/sec. Fluorescence data were collected in real-time at 1.0 sec intervals for the first 60 secs and at 6.0 sec intervals for an additional 120 secs. Responses were measured as peak fluorescence intensity minus basal and where appropriate were expressed as a percentage of a maximum 5-HT-induced response. When the compounds were tested as antagonists against 10 µM 5-HT, they were incubated with the cells for 15 minutes prior to the addition of 5-HT.

The above procedures were used to generate the data shown in Table 2.

TABLE 2

| Compound | Rat Cerebral Cortex 5-HT₂ $IC_{50}$ 5-pt (DOI) | FLIPR 5-HT$_{2a}$ $EC_{50}$ | FLIPR 5-HT$_{2a}$ % $E_{max}$ A7r5 Ca + 2 |
|---|---|---|---|
| Example 1 | 7.26 × 10⁻¹⁰ | 1.88 × 10⁻⁷ | 46.5 |
| Example 2 | 1.18 × 10⁻⁸ | 1.49 × 10⁻⁶ | 26.9 |
| Example 3 | 1.16 × 10⁻⁸ | 1.41 × 10⁻⁶ | 28.4 |
| Example 4 | 2.01 × 10⁻⁹ | 5.80 × 10⁻⁷ | 28.9 |
| Example 5 | 1.70 × 10⁻⁹ | 1.12 × 10⁻⁶ | 38.9 |
| Example 6 | 4.92 × 10⁻⁹ | na | 17.8 |
| Example 7 | 5.72 × 10⁻⁹ | n/a | 17.3 |
| Example 8 | 1.51 × 10⁻⁷ | n/a | 2.6 |
| Example 9 | 2.47 × 10⁻⁸ | n/a | 21.8 |
| Example 10 | 1.64 × 10⁻⁸ | n/a | 20.4 |
| Example 11 | 2.14 × 10⁻⁹ | 6.12 × 10⁻⁷ | 46.4 |
| Example 12 | 4.90 × 10⁻⁹ | 9.11 × 10⁻⁷ | 37.4 |

The compounds of this invention may be prepared by the methods described in Schemes 1–4. The appropriately substituted naphthalene compound (Scheme 1) is treated with dichloromethyl methyl ether in the presence of a Lewis acid such as Tin(IV)chloride in an inert solvent such as dichloromethane at a temperature from −20 to 20° C. Condensation of the resulting aldehyde with nitroethane in the presence of ammonium acetate provides the nitrostyrene. Reduction with a hydride reducing agent such as lithium aluminum hydride results in the formation of the aryl aminopropane.

Scheme 1

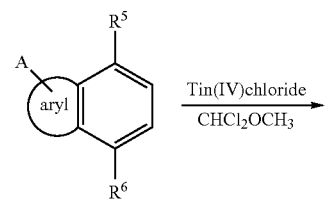

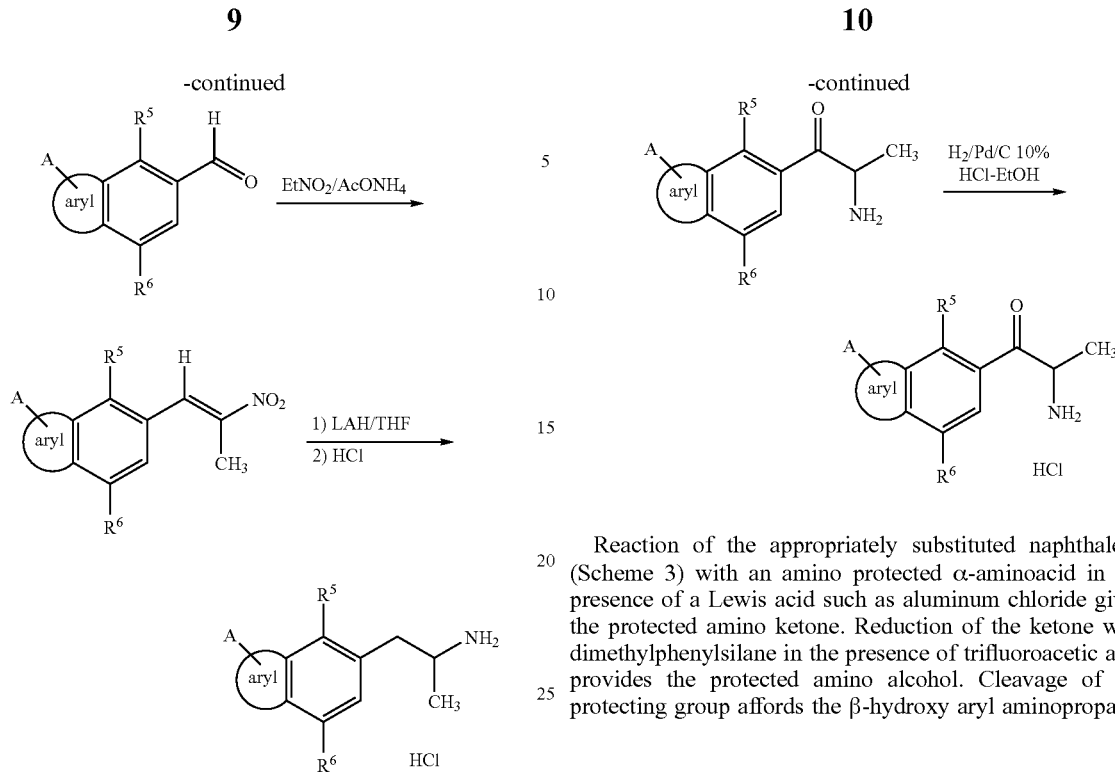

Reaction of the appropriately substituted naphthalene (Scheme 2) with an acyl chloride such as propionyl chloride in the presence of a Lewis acid such as aluminum chloride provides the ketone. Treatment of the ketone with butyl nitrite in the presence of hydrogen chloride in a solvent such as ethyl ether provides the oxime. Hydrogenation in the presence of a catalyst such as 10% Pd/C in a solvent such as ethanol in the presence of acid yields the keto-amine. Hydrogenation of the keto-amine affords the aryl aminopropane.

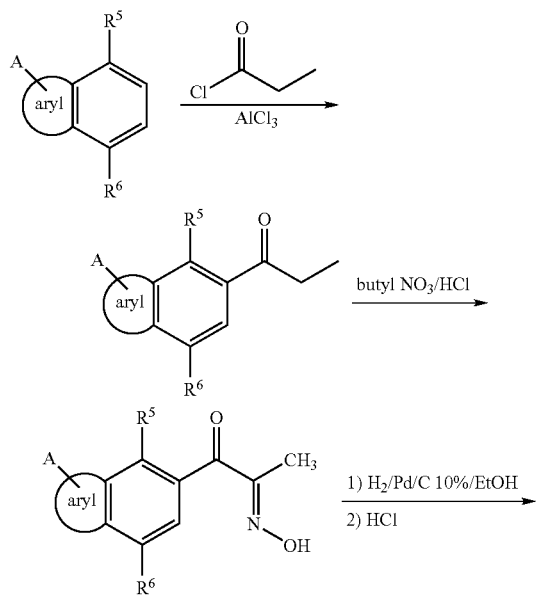

Reaction of the appropriately substituted naphthalene (Scheme 3) with an amino protected α-aminoacid in the presence of a Lewis acid such as aluminum chloride gives the protected amino ketone. Reduction of the ketone with dimethylphenylsilane in the presence of trifluoroacetic acid provides the protected amino alcohol. Cleavage of the protecting group affords the β-hydroxy aryl aminopropane.

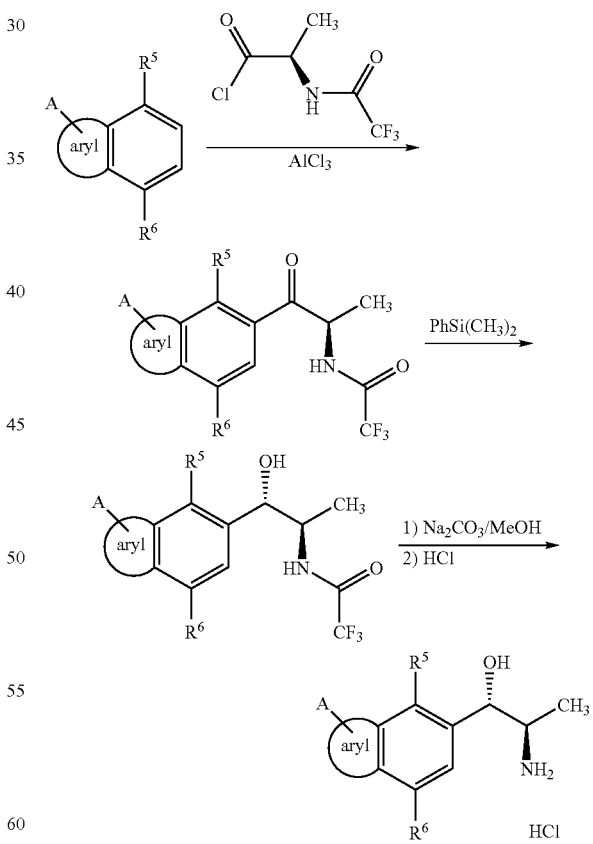

Reaction of the appropriately substituted hydroxy-naphthalene carboxylic acid (Scheme 4) with an alkyating agent such as dimethyl sulfate in the presence of a base such as sodium carbonate in a solvent such as acetone, provides the methoxy ester. Reduction of the ester with a reducing agent such as lithium aluminum hydride provides the benzyl alcohol. Oxidation of the alcohol with a selective oxidizing agent such as pyridinium chlorochromate yields the aldehyde. Using the methods described in Scheme 1 the aldehyde can be converted to the amino-protected naphthalene compound. Treatment of the protected aryl aminopropane with bromine in a solvent such as methylene chloride yields the aryl bromide. Deprotection of the amino group provides the bromoaryl aminopropane.

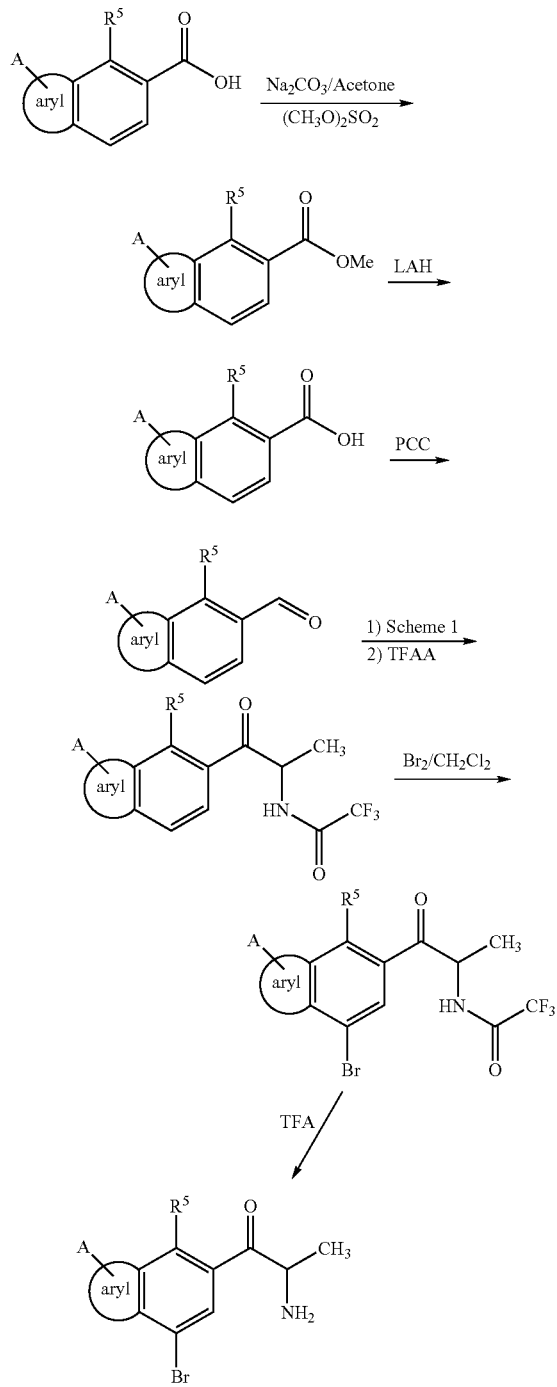

Scheme 4

EXAMPLE 1

2-(1,4-Dimethoxy-naphthalen-2-yl)-1-methylethylamine hydrochloride

Step A. 1,4-dimethoxy-naphthalene-2-carboxaldehyde

To a solution of 1,4-dimethoxy-naphthalene (5 g, 26.6 mmol) in dichloromethane (100 mL) at 0° C. was added dichloromethyl methyl ether (3.66 g, 31.9 mmol) and stannic chloride (13.8 g, 53.1 mmol). The reaction mixture was stirred for 30 min at this temperature, allowed to warm to room temperature and stirred for an additional 30 min. Water (100 mL) was added and the mixture was extracted with dichloromethane (2×100 mL) and the combined extracts dried (MgSO$_4$). The solvent was removed under reduced pressure and the residue was purified by column chromatography (silica gel, ethyl acetate/hexane: 2/8) to give a white solid: $^1$H NMR (DMSO-d$_6$) δ 4.06 (s, 3H, CH3), 4.13 (s, 3H, CH3), 7.14 (s, 1H, Ar—H), 7.82 (m, 2H, Ar—H), 8.29 (m, 2H, Ar—H), 10.54 (s, 1H, CHO).

Step B. 1-(1,4-Dimethoxy-naphthalen-2-yl)-2-nitropropene

To a solution of the product from Step A (0.8 g, 2.93 mmol) in nitroethane (10 mL) was added ammonium acetate (0.45 g, 5.84 mmol). The mixture was stirred at 60° C. overnight. The excess nitroethane was removed and the residue purified by flash chromatography (silica gel, ethyl acetate/hexane: 0.5/9.5) to give 0.5 g of a yellow solid: $^1$H NMR (DMSO-d$_6$) δ 2.45 (s, 3H, CH3), 3.84 (s, 3H, OCH3), 4.00 (s, 3H, OCH3), 6.95 (s, 1H, Ar—H), 7.65 (m, 2H, Ar—H), 8.10 (m, 2H, Ar—H), 8.29 (s, 1H, CH═).

Step C. 2-(1,4-Dimethoxy-naphthalen-2-yl)-1-methylethylamine hydrochloride

The product from Step B (0.5 g, 1.83 mmol) was dissolved in tetrahydrofuran (50 mL). This solution was cooled to 0° C. and then a 1 M solution of lithium aluminum hydride in tetrahydrofuran (9 mL) was added. The reaction mixture was allowed to warm to room temperature and then warmed at reflux for an additional 5 h. The excess lithium aluminum hydride was destroyed by the addition of ethyl acetate and water. The organic material was extracted with dichloromethane (3×50 mL). The combined extracts were dried (MgSO$_4$) and concentrated to give an oil which was dissolved in dry ethyl ether. To this solution was added a 1.0 M solution of hydrogen chloride in diethyl ether (10 mL). A solid formed (200 mg) and was collected by filtration: $^1$H NMR (DMSO-d$_6$) δ 1.15 (d, 3H, CH3), 2.97 (m, 2H, CH2), 3.60 (m, 1H), 3.82 (s, 3H, OCH3), 3.96 (s, 3H, OCH3), 6.85 (s, 1H, Ar—H), 7.96 (d, 2H, Ar—H), 8.12 (d, 2H, Ar—H), 8.15 (bs, NH3+); MS 246 (M+1). Analysis. Calcd. for $C_{15}H_{19}NO_2$·HCl·2 $H_2O$: C, 63.13; H, 7.20; N, 4.91. Found: C, 62.73; H, 7.03; N, 4.87.

EXAMPLE 2

2-Amino-1-(1,4-dimethoxy-naphthalen-2-yl)-propan-1-ol hydrochloride

Step A. 1-(1,4-Dimethoxy-naphthalen-2-yl)-propan-1-one

To a cold solution (ice bath) of 1,4-dimethoxy-naphthalene (5 g, 26.6 mmol) in dichloroethane (100 mL) was added propionyl chloride (2.7 g, 29.3 mmol) followed by aluminum chloride (3.9 g, 29.3 mmol). After the addition was complete, the reaction mixture was allowed to warm to room temperature and stirred for 4 hr. Water (200 mL) was added and the organic material was extracted with dichloromethane (200 mL). The organic extracts were dried (MgSO$_4$) and concentrated to give a residue which was purified by flash chromatography (silica gel, ethyl acetate/hexane: 1/9) to give an oil (1.4 g): $^1$H NMR (DMSO-d$_6$) δ 1.16 (t, 3H, CH$_3$), 3.13 (q, 2H, CH$_2$), 3.87 (s, 3H, OCH$_3$), 3.98 (s, 3H, OCH3), 7.02 (s, 1H, Ar—H), 7.67 (m, 2H, Ar—H), 8.10 (d, 2H, Ar—H); MS 245 (M+1).

Step B. 1-(1,4-Dimethoxy-naphthalen-2-yl)-propane-1,2-dione 2-oxime

The product from Step A (1.28 g, 5.24 mmol) was dissolved in ethyl ether (50 mL), anhydrous hydrogen chloride gas was added through this solution at moderate rate for 5 min. Butyl nitrite (0.68 mL, 5.77 mmol) was then added dropwise. Hydrogen chloride bubbling was continued for an additional 10 min. after addition of butyl nitrite was completed, the reaction mixture was then stirred at room temperature for 4 hr. The volatiles were removed by evaporation under vacuum and the residue was purified by flash chromatography (silica gel, ethyl acetate/hexane: 0.5/9.5) to give an oil (0.8 g): MS 274 (M+1).

Step C. 2-Amino-1-(1,4-dimethoxy-naphthalen-2-yl)-propan-1-ol hydrochloride

The product from Step B (0.8 g, 2.93 mmol) was dissolved in ethanol (50 mL). Hydrogen chloride gas was bubbled through this solution for 3 min and then 10% Pd/C (200 mg) was added. This mixture was hydrogenated using a Parr apparatus at 50 psi overnight. The catalyst was removed by filtration through a filter-aide and the filtrate was concentrated to give a solid. Recrystallized from ethyl acetate gave a white solid (200 mg): $^1$H NMR (DMSO-d$_6$) δ 1.03 (d, 3H, CH$_3$), 3.40 (m, 1H), 3.89 (s, 3H, OCH$_3$), 3.99 (s, 3H, OCH$_3$), 5.37 (d, 1H), 6.19 (bs, 1H), 7.02 (s, 1H, Ar—H), 7.65 (m, 2H, Ar—H), 8.09 (dd, 2H, Ar—H). 8.19 (bs, NH3+); MS 262 (M+1). Analysis. Calcd. for C$_{15}$H$_{19}$NO$_3$.HCl.0.9 H$_2$O: C, 57.38; H, 7.00; N, 4.46. Found: C, 57.36; H, 6.60; N, 4.52.

EXAMPLE 3

(1S,2R)-2-Amino-1-(1,4-dimethoxy-naphthalen-2-yl)-propan-1-ol hydrochloride

Step A. N-[(R)-2-(1,4-Dimethoxy-naphthalen-2-yl)-1-methyl-2-oxo-ethyl]-2,2,2-trifluoro-acetamide To a suspension of AlCl$_3$ (3.8 g, 28.6 mmol) in dichloromethane (100 mL) was added a solution of 1,4-dimethoxynaphthalene (4.88 g, 25.9 mmol) in dichloromethane (50 mL). To this mixture was added a solution of (R)-N-trifluoroacetylalanine (16 g, 86.5 mmol) in CH$_2$Cl$_2$ (50 mL); this mixture was stirred at room temperature for 3 h. The reaction mixture was poured slowly into ice (200 g) to quench the reaction and the organic layer was separated and dried (MgSO$_4$). The solvent was evaporated and the residue was purified by flash chromatography (silica gel, ethyl acetate/hexane: 1/9) to give a yellow oil (3 g): $^1$H NMR (DMSO-d$_6$) δ 1.24 (d, 3H, CH$_3$), 3.93 (s, 3H, OCH$_3$), 4.01 (s, 3H, OCH$_3$), 5.51 (m, 1H), 6.99 (s, 1H, Ar—H), 7.96 (m, 2H, Ar—H), 8.17 (m, 2H, Ar—H), 9.83 (d, NH); MS 356 (M+1).

Step B. (1S,2R)-2-Amino-1-(1,4-dimethoxy-naphthalen-2-yl)-propan-1-ol hydrochloride The product from Step A (2.2 g, 6.19 mmol) was dissolved in trifluoroacetic acid (30 mL) at −5° C. To this cold solution (ice bath-acetone) was added dimethylphenylsilane (1.00 g, 7.44 mmol) and the reaction mixture was stirred at this temperature until all starting material was consumed (3 h). Excess TFA was removed and the residue was dissolved in methanol (50 mL) and water (10 mL), sodium carbonate (5 g, 36.2) was added and the mixture was refluxed for 2 h. The volatiles were removed and the residue was diluted with water. This mixture was extracted with dichloromethane (3×100 mL), dried (MgSO$_4$) and concentrated to give an oil (1.6 g). The oil was dissolved in diethyl ether and transformed to the hydrochloride salt by adding 10 mL of 1 M hydrogen chloride solution in diethyl ether: $^1$H NMR (DMSO-d$_6$) δ 1.03 (d, 3H, CH$_3$), 3.43 (m, 1H), 3.84 (s, 3H, OCH$_3$), 3.95 (s, 3H, OCH$_3$), 5.33 (m, 1H), 6.16 (bs, 1H, OH), 7.04 (s, 1H, Ar—H), 7.60 (m, 2H, Ar—H), 7.97 (dd, 2H, Ar—H). 8.19 (bs, NH3+); MS 262 (M+1). Analysis. Calcd. for C$_{15}$H$_{19}$NO$_3$.HCl: C, 60.50; H, 6.77; N, 4.70. Found: C, 60.26; H, 6.76; N, 4.66.

EXAMPLE 4

2-(1-Methoxy-naphthalen-2-yl)-1-methylethylamine hydrochloride

Step A. Methyl 1-methoxy-naphthalene-2-carboxylate

To a solution of 1-hydroxy-naphthalene-2-carboxylic acid (5 g, 26.6 mmol) in acetone (100 mL) was added potassium carbonate (11 g, 79.72 mmol) followed by dimethyl sulfate (7.38 g, 58.46 mmol). The reaction mixture was refluxed overnight and then diluted with ethyl acetate (200 mL) and washed with water. The organic layer was dried (MgSO$_4$), and the solvent was removed to give an oil (5.2 g): $^1$H NMR (CDCl$_3$) δ 3.98 (s, 3H, CH$_3$), 4.06 (s, 3H, CH$_3$), 7.59 (m, 3H, Ar—H), 7.85 (m, 2H, Ar—H), 8.25 (m, 1H, Ar—H); MS 217 (M+1).

Step B. 2-Hydroxymethyl-1-methoxy-naphthalene

The product of Step A (4.5 g, 20.83 mmol) was dissolved in anhydrous tetrahydrofuran (100 mL) and cooled to 0° C. To this solution was added a 1 M solution of lithium aluminum hydride in tetrahydrofuran (31 mL). The mixture was stirred at this temperature for 30 min, allowed to warm up to room temperature, and stirred for an additional 30 min. Ethyl acetate (200 mL) was then added carefully to the reaction mixture to destroy the excess of lithium aluminum hydride. The mixture was then diluted with a 1 M solution of aqueous hydrogen chloride (100 mL), the organic layer was separated, dried (MgSO$_4$), and concentrated to give an oil (4.1 g) which solidified: $^1$H NMR (CDCl$_3$) δ 3.97 (s, 3H, CH$_3$), 4.89 (s, 2H, CH$_2$), 7.51 (m, 3H, Ar—H), 7.60 (m, 1H, Ar—H), 7.82 (m, 1H, Ar—H), 8.07 (m, 1H, Ar—H); MS (GC/MS) 188.

Step C. 1-methoxy-2-naphthalenecarboxaldehyde

The product from Step B (4 g, 27.28 mmol) was dissolved in dichloromethane (100 mL) and cooled to 0° C. To this solution was added pyridinium chlorochromate (5.5 g, 25.53 mmol) and the reaction was stirred at this temperature for 1 h. The reaction mixture was washed with 1 M aqueous solution of hydrogen chloride. The organic layer was separated, dried (MgSO$_4$), and concentrated to give an oil, which was purified by flash chromatography (silica gel, ethyl acetate/hexane: 1/9): $^1$H NMR (CDCl$_3$) δ 4.15 (s, 3H, CH$_3$), 7.61 (m, 3H, Ar—H), 7.87 (m, 2H, Ar—H), 8.28 (m, 1H, Ar—H), 10.61 (s, 1H, CHO); MS 191 (M+NH$_4^+$).

Step D. 2-(1-Methoxy-naphthalen-2-yl)-1-methylethylamine hydrochloride

The product from Step C (3.04 g, 18.3 mmol) was dissolved in ethanol (50 mL), ammonium acetate (1.55 g, 20.10 mmol) was added followed by nitroethane (2.75 g, 36.5 mmol). The reaction mixture was stirred at 70° C. for 3 h and then the solvent was removed. The residue was dissolved in ethyl acetate (100 mL) and washed with water (2×100 mL). The organic layer was dried (MgSO$_4$) and concentrated to give a solid, which was dissolved in anhydrous tetrahydrofuran (100 mL) and cooled to 0° C. To this solution, a 1 M solution of lithium aluminum hydride in tetrahydrofuran (73 mL) was added and the reaction mixture allowed to warm to room temperature and stirred for 2 h followed by heating at reflux for an additional 2 h. Excess lithium aluminum hydride was consumed by adding ethyl acetate (50 mL) and then water (400 mL). The organic material was extracted with dichloromethane, dried (MgSO$_4$), and concentrated to give an oil which was transformed to hydrochloride salt by adding 1 M solution of hydrogen chloride in diethyl ether. The white solid was collected by filtration: $^1$H NMR (DMSO-d) δ 1.14 (d, 3H, CH$_3$), 2.94 (m, 2H, CH$_2$), 3.52 (m, 1H, CH), 3.89 (s, 3H, OCH$_3$), 7.38–8.06 (m, 6H, Ar—H), 8.19 (bs, NH3+); MS 216 (M+1). Analysis. Calcd. for C$_{14}$H$_{17}$NO.HCl.0.3 H$_2$O: C, 65.39; H, 7.21; N, 5.56. Found: C, 65.16; H, 7.07; N, 5.42.

EXAMPLE 5

2-(4-Bromo-1-methoxy-naphthalen-2-yl)-1-methylethylamine hydrochloride

To a solution of the product from Example 4 (1.2 g, 4.78 mmol) and TEA (0.97 g, 9.56 mmol) in dichloromethane (100 ml) at 0° C. was added trifluoroacetic anhydride (1.2 g, 5.74 mmol). The reaction mixture was stirred at 0° C. for 1 h and evaporated to a residue, which was filtered through silica (ethyl acetate/hexane: 2/8). The fractions containing the protected amine were combined and concentrated to a residue that was dissolved in acetic acid (5 mL) and cooled to 0° C. Bromine (0.91 g, 5.74 mmol) was added and the reaction mixture stirred at this temperature for 30 min. The solid that formed was collected by filtration and dissolved in a mixture of methanol in water (1:1, 20 mL). To this solution was added 1 N aqueous sodium hydroxide (3 mL) and the mixture was stirred at room temperature overnight. Volatiles were evaporated and the desired compound was extracted with dichloromethane and transformed to hydrochloride salt, which was recrystallized from methanol-diethyl ether. Analysis. Calcd. for C$_{14}$H$_{16}$BrNO.HCl.0.2 CH$_3$OH: C, 65.39; H, 7.21; N, 5.56. Found: C, 65.16; H, 7.07; N, 5.42.

EXAMPLE 6

2-amino-1-(3,8-dimethoxy-naphthalen-2-yl)-propan-1-ol hydrochloride

This compound was prepared from 3,8-dimethoxy-naphthalene by the same procedure described for example 1: $^1$H NMR (DMSO-d$_6$) δ 1.11 (d, 3H, CH3), 2.90 (m, 2H), 3.49 (m, 1H), 3.91 (s, 3H), 3.94 (s, 3H), 6.80 (m, 1H, Ar—H), 7.31 (s, 1H, Ar—H), 7.38 (m, 2H, Ar—H), 7.92 (s, 1H, Ar—H), 8.09 (bs, 3H, NH3+); Analysis calcd. for C$_{15}$H$_{19}$NO$_2$.HCl.5 H$_2$O. Calc. C, 61.96; H, 7.28; N, 4.82. Found: C, 62.26; H, 7.10; N, 4.81.

EXAMPLE 7

2-(1-hydroxy-naphthalen-2-yl)-1-methylethylamine hydrochloride

A solution of 2-(1-methoxy-naphthalen-2-yl)-1-methylethylamine hydrochloride (0.1 g, 0.40 mmol) and HBr 48% was refluxed for 3 h. The reaction mixture was concentrated under vacuum, the residue was washed with hexane and ether and then collected by filtration: $^1$H NMR (DMSO-d) δ 1.14 (d, 3H, CH$_3$), 2.86–3.11 (m, 2H, CH$_2$), 3.47 (m, 1H, CH), 7.25 (d, 1H, Ar—H), 7.47 (m, 2H, Ar—H), 7.83 (m, 4H, 1Ar—H+NH3+); 8.24 (m, 1H, Ar—H), 9.36 (s, OH); MS 202 (M+1). Analysis. Calcd. for C$_{13}$H$_{15}$NO.HBr.0.5 H$_2$O: C, 53.62; H, 5.88; N, 4.81. Found: C, 53.53; H, 5.56; N, 4.77.

EXAMPLE 8

2-(5,8-dimethoxy-naphthalen-2-yl)-1-methylethylamine hydrochloride

This compound was prepared from 5,8-dimethoxy-naphthalene by the same procedure described for example 1.

EXAMPLE 9

2-amino-1-(1,4-dimethoxy-naphthalen-2-yl)-propan-1-one hydrochloride

To a solution of 1-(1,4-dimethoxynaphthalen-2-yl)-propane-1,2-dione 2-oxime (1 g, 3.66 mmol, Example 2, Step B) in 1 M hydrogen chloride in ethanol (50 mL) was added Pd/C 10% (100 mg), The mixture was hydrogenated on a Parr hydrogenator apparatus under 40–50 psi pressure for 12 h. The catalyst was separated by filtration and the solvent removed in vacuo to give a white solid: $^1$H NMR (DMSO-d) δ 1.14 (d, 3H, CH$_3$), 3.96 (s, 3H, OH$_3$), 4.01 (s, 3H, OCH$_3$), 5.03 (m, 1H, CH), 7.08 (s, 1H, Ar—H), 7.73 (m, 2H, Ar—H), 8.19 (m, 2H, Ar), 8.50 (bs, 3H, NH3+); Analysis calcd. for C$_{15}$H$_{17}$NO$_3$.HCl.0.2 H$_2$O: C, 53.62; H, 5.88; N, 4.81. Found: C, 53.53; H, 5.56; N, 4.77.

EXAMPLE 10

2-(naphthalen-2-yl)-1-methylethylamine hydrochloride

This compound was prepared from the commercially available naphthalene-2-aldehyde using the same procedure described for the preparation of example 1: $^1$H NMR (DMSO-d$_6$) δ 1.15 (d, 3H, CH3), 2.86 (dd, 1H), 3.11 (dd, 1H), 3.54 (m, 1H), 7.42–7.59 (m, 3H, Ar—H), 7.79 (s, 1H, Ar—H), 7.84–8.03 (m, 3H, Ar—H), 8.15 (bs, 3H, NH3+); MS 186 (M+1). Analysis calcd. for C$_{13}$H$_{15}$N.HCl.0.2 H$_2$O: Analysis calcd. for C13H15N, 69.79; H, 7.39; N, 6.26. Found: C, 69.63; H, 7.17; N, 6.26.

EXAMPLE 11

2-(4-methoxy-naphthalen-2-yl)-1-methylethylamine hydrochloride

This compound was prepared using the same procedure described for the preparation of example 1, starting material, 4-methoxy-naphthyl-2-carbaldehyde, was prepared as described by Horii, Z. et al *Chem. Pharma. Bull.* 1971, 19, 1250: $^1$H NMR (DMSO-d$_6$) δ 1.16 (d, 3H, CH3), 2.85 (dd, 1H), 3.15 (dd, 1H), 3.60 (m, 1H), 3.96 (s, 3H, OCH3), 6.87 (s, 1H, Ar—H), 7.29 (s, 1H, Ar—H), 7.49 (m, 2H, Ar—H), 7.78 (dd, 1H, Ar—H), 8.15 (m, 4H, 1Ar—H+NH3+); MS 216 (M+1). Analysis calcd. for C$_{14}$H$_{17}$NO.HCl: C, 66.79; H, 7.21; N, 5.56. Found: C, 66.86; H, 7.41; N, 5.59.

EXAMPLE 12

2-(1-Bromo-4-methoxy-naphthalen-2-yl)-1-methyl-ethylamine hydrochloride

To a cold heterogeneous solution (ice bath) of 2-(4-methoxy-naphthalen-2-yl) 1-methyl-ethylamine hydrochloride (0.10 g, 0.39 mmol, Example 11) in dichloromethane, was added bromine (0.07 g, 0.43 mmol) via syringe. After 1 h the volatiles were evaporated and the residue was partitioned in a mixture of ethyl acetate (20 mL) and a saturated aqueous solution of bicarbonate (20 mL). The organic layer was separated, dried (MgSO$_4$), and concentrated in vacuo. The residue was dissolved in ethyl ether (20 mL) and the free amine was transformed to its correspondent hydrochloride salt by adding 1 M solution of hydrogen chloride in ethyl ether. The solid formed was collected by filtration (80 mg): $^1$H NMR (DMSO-d$_6$) δ 1.21 (d, 3H, CH3), 3.24 (m, 2H), 3.60 (m, 11H), 3.66 (m, 1H), 4.02 (s, 3H, OCH3), 7.03 (s, 1H, Ar—H), 7.48–7.75 (m, 2H, Ar—H), 7.96 (m, 3H, NH3+), 8.17 (m, 2H, Ar—H); MS 296 (M+1).

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A compound represented by Formula I:

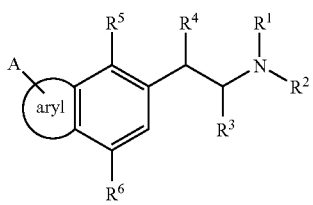

wherein $R^1$ and $R^2$ are independently chosen from hydrogen or an alkyl group and $R^3$ is $C_{1-3}$ alkyl;
$R^4$ is H or $OR^1$;
$R^5$ is $OCON(R^1,R^2)$, $OCOR^1$, or $OR^7$;
$R^6$ is H, $OR^7$, $CONR^1R^2$, $CH_2OR^7$, $CO_2R^1R^2$, $N(R^1R^2)$, with the proviso that both $R^5$ and $R^6$ are not H;
Aryl is at least one aryl group;
A is chosen from hydrogen, an alkyl group, $C(=O)OR^7$, $OR^7$, $CR^7$, $C(=O)NR^1R^2$, $SO_2(NR^1R^2)$, halogen, or $CF_3$; and
$R^7$ is H, a substituted or unsubstituted alkyl group, $C_{1-3}CONR^1R^2$, $C_{1-3}N(R^1R^2)$, $C_{1-3}CO_2H$, or $C_{1-3}CO_2C_{1-3}$alkyl, with the proviso that when $R^1$, $R^2$, and $R^4$ each are hydrogen, $R^5$ and $R^6$ do not represent $OR^7$ at the same time.

2. The compound of claim 1, wherein $R^1$ and $R^2$ are independently chosen from hydrogen H or $C_{1-3}$ alkyl and $R^3$ is $C_{1-3}$alkyl;
$R^4$ is H or $OR^1$;
$R^5$ is $OCON(R^1,R^2)$, $OCOR^1$, or $OR^7$;
$R^6$ is H, $OR^7$, $CONR^1R^2$, $CH_2OR^7$, $CO_2R^1R^2$, $N(R^1R^2)$, with the proviso that both $R^5$ and $R^6$ are not H;
Aryl is phenyl, pyridinyl, or thienyl;
A is chosen from hydrogen, $C_{1-4}$alkyl, $C(=O)OR^7$; $OR^7$, $CR^7$, $C(=O)NR^1R^2$, $SO_2(NR^1R^2)$, halogen, or $CF_3$;
$R^7$ is H, $C_{1-3}$alkyl, $C_{1-3}CONR^1R^2$, $C_{1-3}N(R^1R^2)$, $C_{1-3}CO_2H$, $C_{1-3}CO_2C_{1-3}$alkyl, or $C_{1-3}$alkyl substituted with hydroxyl, $C_{1-3}CO_2C_{1-3}$alkyl, $C_{1-3}CON(C_{1-3}$alkyl)$_2$, $C(=NH)NH_2$, $NHC(=NH)NH_2$, or $C_{1-3}$alkoxy.

3. A method of controlling normal or elevated intraocular pressure comprising administering a pharmaceutically effective amount of a composition comprising at least one compound of claim 1.

4. The method of claim 3, wherein $R^1$ and $R^2$ are independently chosen from hydrogen or $C_{1-3}$ alkyl and $R^3$ is $C_{1-3}$alkyl;
$R^4$ is H or $OR^1$;
$R^5$ is $OCON(R^1,R^2)$, $OCOR^1$, or $OR^7$;
$R^6$ is H, $OR^7$, $CONR^1R^2$, $CH_2OR^7$, $CO_2R^1R^2$, $N(R^1R^2)$, with the proviso that both $R^5$ and $R^6$ are not H;
Aryl is phenyl, pyridinyl, or thienyl;
A is chosen from hydrogen, $C_{1-4}$alkyl, $C(=O)OR^7$; $OR^7$, $CR^7$, $C(=O)NR^1R^2$, $SO_2(NR^1R^2)$, halogen, or $CF_3$;
$R^7$ is H, $C_{1-3}$alkyl, $C_{1-3}CONR^1R^2$, $C_{1-3}N(R^1R^2)$, $C_{1-3}CO_2H$, $C_{1-3}CO_2C_{1-3}$alkyl, or $C_{1-3}$alkyl substituted with hydroxyl, $C_{1-3}CO_2C_{1-3}$alkyl, $C_{1-3}CON(C_{1-3}$alkyl)$_2$, $C(=NH)NH_2$, $NHC(=NH)NH_2$, or $C_{1-3}$alkoxy.

5. A method for the treatment of glaucoma comprising administering a pharmaceutically effective amount of a composition comprising at least one compound of claim 1.

6. The method of claim 5, wherein $R^1$ and $R^2$ are independently chosen from hydrogen or $C_{1-3}$ alkyl and $R^3$ is $C_{1-3}$alkyl;
$R^4$ is H or $OR^1$;
$R^5$ is $OCON(R^1,R^2)$, $OCOR^1$, or $OR^7$;
$R^6$ is H, $OR^7$, $CONR^1R^2$, $CH_2OR^7$, $CO_2R^1R^2$, $N(R^1R^2)$, with the proviso that both $R^5$ and $R^6$ are not H;
Aryl is phenyl, pyridinyl, or thienyl;
A is chosen from hydrogen, $C_{1-4}$alkyl, $C(=O)OR^7$; $OR^7$, $CR^7$, $C(=O)NR^1R^2$, $SO_2(NR^1R^2)$, halogen, or $CF_3$;
$R^7$ is H, $C_{1-3}$alkyl, $C_{1-3}CONR^1R^2$, $C_{1-3}N(R^1R^2)$, $C_{1-3}CO_2H$, $C_{1-3}CO_2C_{1-3}$alkyl, or $C_{1-3}$alkyl substituted with hydroxyl, $C_{1-3}CO_2C_{1-3}$alkyl, $C_{1-3}CON(C_{1-3}$alkyl)$_2$, $C(=NH)NH_2$, $NHC(=NH)NH_2$, or $C_{1-3}$alkoxy.

7. A pharmaceutical composition comprising the compound of claim 1 and at least one carrier.

8. A pharmaceutical composition comprising the compound represented by Formula I:

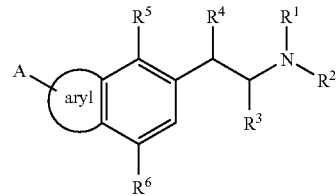

wherein $R^1$ and $R^2$ are independently chosen from hydrogen or an alkyl group and $R^3$ is $C_{1-3}$ alkyl:
$R^4$ is H or $OR^1$;
$R^5$ is $OCON(R^1,R^2)$, $OCOR^1$, or $OR^7$;
$R^6$ is H, $OR^7$, $CONR^1R^2$, $CH_2OR^7$, $CO_2R^1R^2$, $N(R^1R^2)$, with the proviso that both $R^5$ and $R^6$ are not H;
Aryl is at least one aryl group;
A is chosen from hydrogen, an alkyl group, $C(=O)OR^7$, $OR^7$, $CR^7$, $C(=O)NR^1R^2$, $SO_2(NR^1R^2)$, halogen, or $CF_3$; and $R^7$ is H, a substituted or unsubstituted alkyl group, $C_{1-3}CONR^1R^2$, $C_{1-3}N(R^1R^2)$, $C_{1-3}CO_2H$, or $C_{1-3}CO_2C_{1-3}$alkyl, and at least one ophthalmologically acceptable carrier.

9. The composition of claim 8, wherein
$R^1$ and $R^2$ are independently chosen from hydrogen or $C_{1-3}$ alkyl and $R^3$ is $C_{1-3}$alkyl;
$R^4$ is H or $OR^1$;
$R^5$ is $OCON(R^1,R^2)$, $OCOR^1$, or $OR^7$;
$R^6$ is H, $OR^7$, $CONR^1R^2$, $CH_2OR^7$, $CO_2R^1R^2$, $N(R^1R^2)$, with the proviso that both $R^5$ and $R^6$ are not H;
Aryl is phenyl, pyridinyl, or thienyl;
A is chosen from hydrogen, $C_{1-4}$alkyl, $C(=O)OR^7$; $OR^7$, $CR^7$, $C(=O)NR^1R^2$, $SO_2(NR^1R^2)$, halogen, or $CF_3$; and
$R^7$ is H, $C_{1-3}$alkyl, $C_{1-3}CONR^1R^2$, $C_{1-3}N(R^1R^2)$, $C_{1-3}CO_2H$, $C_{1-3}CO_2C_{1-3}$alkyl, or $C_{1-3}$alkyl substituted with hydroxyl, $C_{1-3}CO_2C_{1-3}$alkyl, $C_{1-3}CON(C_{1-3}$alkyl$)_2$, $C(=NH)NH_2$, $NHC(=NH)NH_2$, or $C_{1-3}$alkoxy.

10. A method of controlling normal or elevated intraocular pressure comprising administering to a subject a pharmaceutically effective amount of the composition of claim 8.

11. The method of controlling normal or elevated intraocular pressure comprising administering to a subject a pharmaceutically effective amount of the composition of claim 9.

12. A method for the treatment of glaucoma comprising administering to a subject in need thereof a pharmaceutically effective amount of the composition of claim 8.

13. The method for the treatment of glaucoma comprising administering to a subject in need thereof a pharmaceutically effective amount of the composition of claim 9.

* * * * *